United States Patent [19]

Tanaka

[11] 4,183,139
[45] Jan. 15, 1980

[54] METHOD OF MARKING DENTAL CONTACT POINTS

[76] Inventor: Asami Tanaka, 4840 Foster St., Skokie, Ill. 60077

[21] Appl. No.: 870,654

[22] Filed: Jan. 19, 1978

[51] Int. Cl.² .............................................. A61C 9/00
[52] U.S. Cl. ................................................... 32/19
[58] Field of Search ........................................... 32/19

[56] References Cited

U.S. PATENT DOCUMENTS

| | | | |
|---|---|---|---|
| 2,171,759 | 9/1939 | Meyer | 32/2 |
| 3,707,771 | 1/1973 | Guerra | 32/19 |
| 3,918,160 | 11/1975 | Friedman | 32/19 |
| 3,959,881 | 6/1976 | Kokal, Jr. | 32/19 |

FOREIGN PATENT DOCUMENTS 51-865363  9/1976  Japan ........................................... 32/19

*Primary Examiner*—Louis G. Mancene
*Assistant Examiner*—John J. Wilson
*Attorney, Agent, or Firm*—Neuman, Williams, Anderson & Olson

[57] ABSTRACT

A method is provided of utilizing a plurality of transferable coatings of contrasting colors for marking contact points at predetermined areas on the occlusal surface of a dental restorative. A coating of each color is applied to predetermined areas of the occlusal surface of a tooth impression molding. The coated surface is then brought into occluding relation with a dental restorative whereupon a portion of the previously applied coating in each predetermined area is transferred to the corresponding predetermined area of the restorative occlusal surface only at each contact point located within said corresponding predetermined area.

12 Claims, 7 Drawing Figures

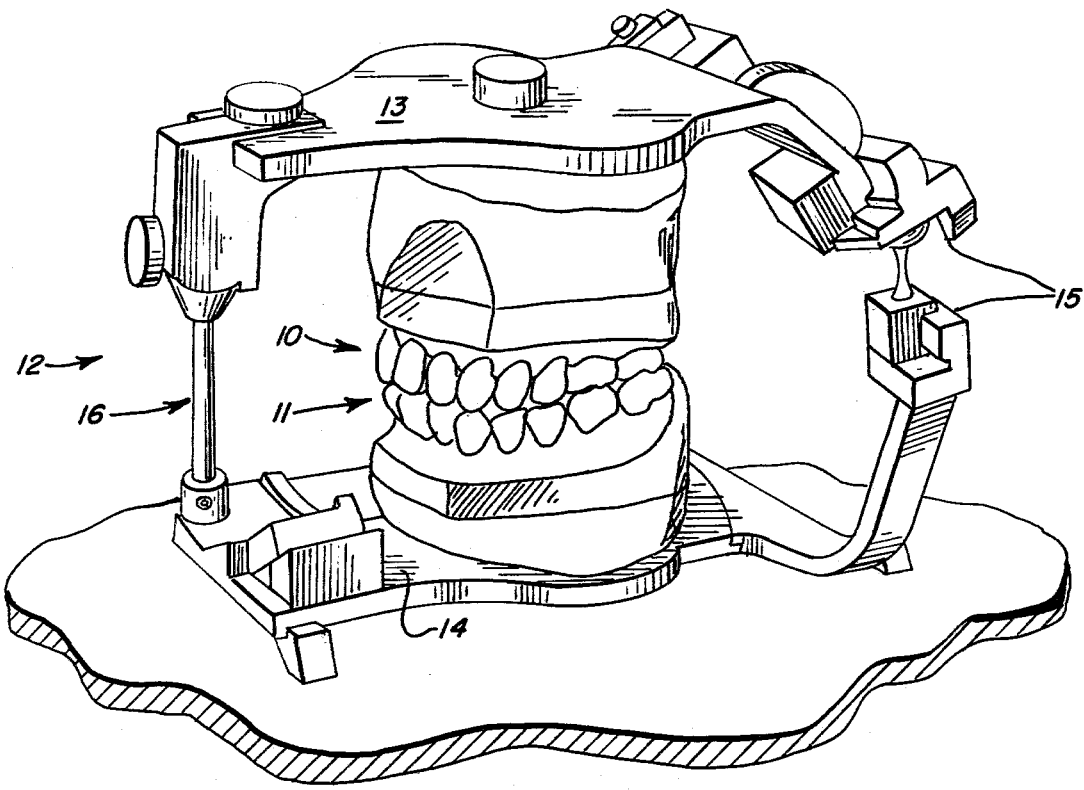
FIG. 1
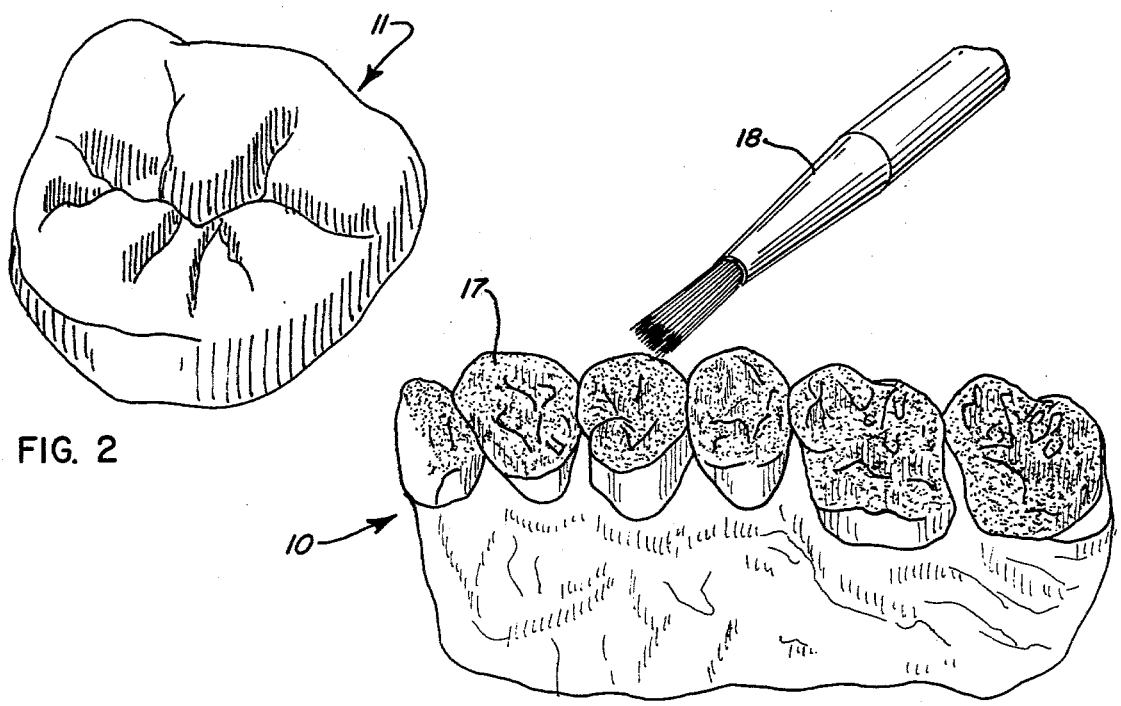
FIG. 2
FIG. 3

METHOD OF MARKING DENTAL CONTACT POINTS

BACKGROUND OF THE INVENTION

In preparing various types of dental restoratives from mouth impressions, difficulty has oftentimes been experienced in accurately contouring the occlusal surface of the dental restorative. In an effort to facilitate such contouring, various methods have heretofore been proposed which, however, have been beset with one or more of the following shortcomings: (a) strips or ribbons, or other similar material, were inserted between the occlusal surfaces in order to determine the contact points; such strips, ribbons or the like, however, because of their thickness prevented the surfaces from attaining a properly occluding relationship; furthermore, such strips, ribbons or the like prevented visual observance of the biting contact between the molding and dental restorative; (b) the coating applied to one of the occlusal surfaces quickly became dry and brittle and while in such a state made it extremely difficult to accurately mark the contact points between the occlusal surfaces; (c) the coating caused an inordinate amount of staining of certain areas of the restorative occlusal surface whereby subsequent removal of the stain therefrom was a difficult and awkward manipulation; and (d) practicing of the method was a complex, time-consuming and oftentimes ineffective operation requiring the talents of one having a high degree of dexterity.

SUMMARY OF THE INVENTION

Thus, it is an object of the invention to provide a method of facilitating accurate contouring of the occlusal surface of a dental restorative which avoids the aforenoted shortcomings.

It is a further object of the invention to provide an improved method of the type described, which enables a dental technician or dentist to readily locate and accurately correct contour imperfections which exist on the occlusal surface of a dental restoration.

It is a still further object of the invention to provide an improved method of the type described which utilizes a plurality of transferable coatings of contrasting colors to identify particular types of contact between occluding surfaces.

It is a still further object of the invention to provide an improved method of the type described wherein the various transferable coatings applied to one occlusal surface will remain in an operative state regardless of the number of times the coated surface is brought into contact with a second occlusal surface.

It is a still further object of the invention to provide an improved method of the type described wherein the coatings applied to one of the occlusal surfaces are of nominal thicknesses and thereby do not impair an accurate occluding relationship between the teeth surfaces.

It is a still further object of the invention to provide a method of the type described which facilitates the accurate fabrication of a procelain crown or pontic.

It is a still further object of the invention to provide a method of the type described which facilitates correcting of certain areas of an occlusal surface where overgrinding of such areas has occurred.

It is an additional object of the invention to provide a method of the type described which may be utilized to check undesirable interference points between occluding teeth during certain jaw movements and/or relations.

Further and additional objects will appear from the description, accompanying drawings and appended claims.

In accordance with one embodiment of the invention a method is provided for marking contact points on the occlusal surface of one tooth of a pair of occluding teeth. The method utilizes a plurality of transferable coatings of contrasting colors which are applied to predetermined areas on the occlusal surface of a first tooth of the pair. Subsequent to the application of one or more coatings, the teeth are brought into occluding relation whereby a portion of each coating applied in a predetermined area is transferred to the corresponding predetermined area of the occlusal surface of the other tooth of the pair only at the contact points located within the corresponding predetermined area.

DESCRIPTION

For a more complete understanding of the invention reference should be made to the drawings wherein:

FIG. 1 is a fragmentary perspective view of a full mouth impression molding and a dental restoration, both being accommodated in an articulating device and shown in occluding relation.

FIG. 2 is an enlarged fragmentary perspective view of a single porcelain crown showing the occlusal surface thereof.

FIG. 3 is an enlarged fragmentary perspective view showing one way of applying a coating of a first contrasting color to the occlusal surface of the upper full mouth impression molding, illustrated in FIG. 1.

Figure 4:
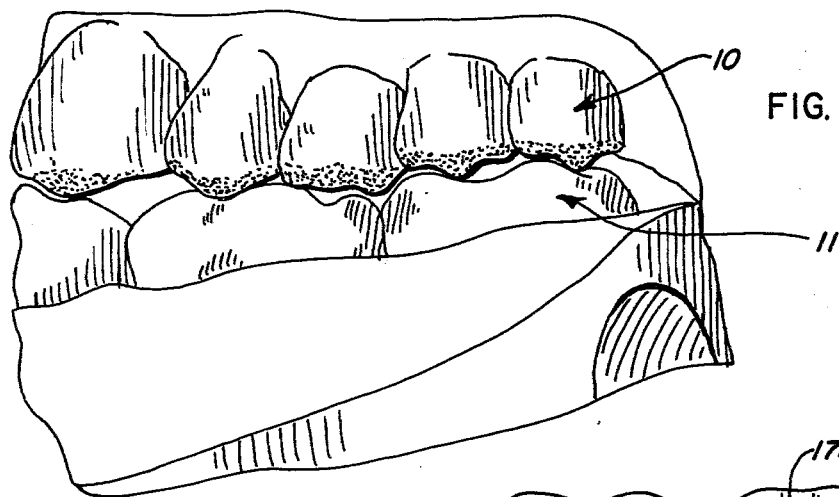
FIG. 4 is an enlarged fragmentary side elevational view showing the upper full mouth impression molding of FIG. 3 with the coating applied thereto in occluding relation with the porcelain crowns of a lower full mouth dental restorative.
Figure 5:
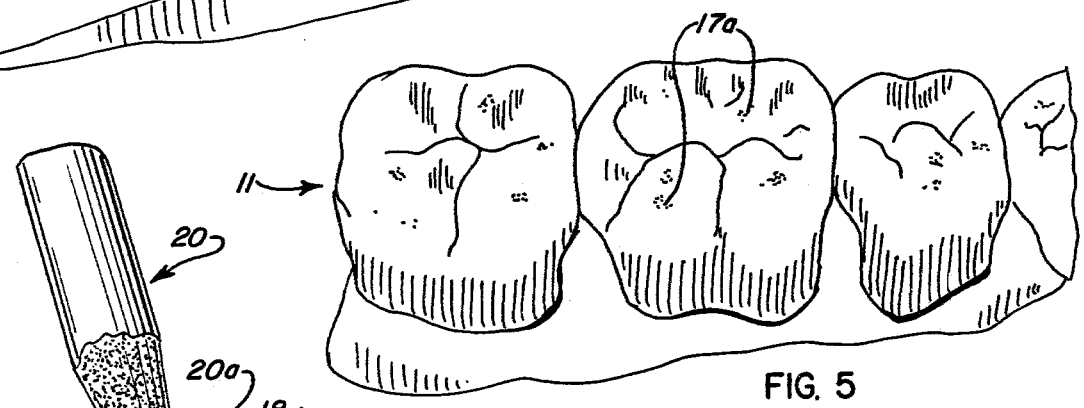
FIG. 5 is an enlarged fragmentary perspective top view of the occlusal surface of the porcelain crowns of the lower full mouth dental restorative of FIG. 4 subsequent to the latter being released from the occluding relationship shown in FIG. 4 and with the contact points on the crown occlusal surface being marked by transferred portions of the coating.
Figure 6:
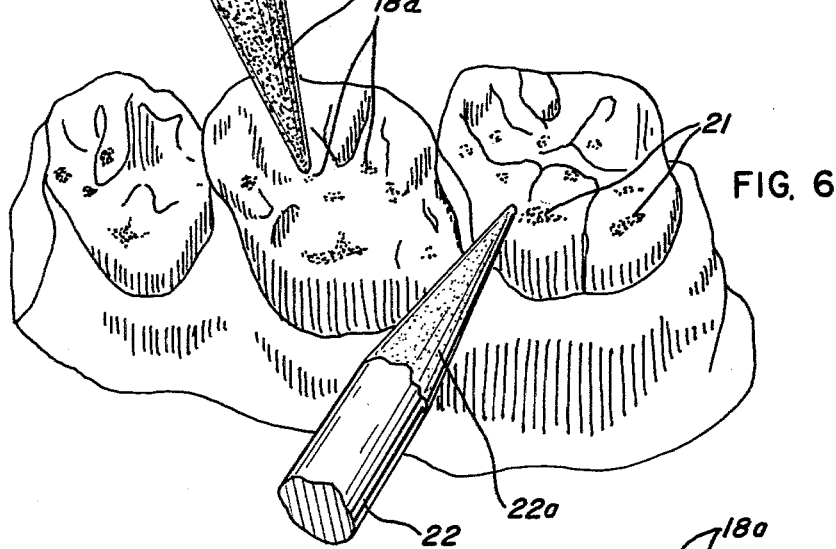
FIG. 6 is an enlarged fragmentary perspective view similar to FIG. 3 but showing second and third coatings being applied to predetermined areas on the occlusal surface of the upper impression molding.
Figure 7:
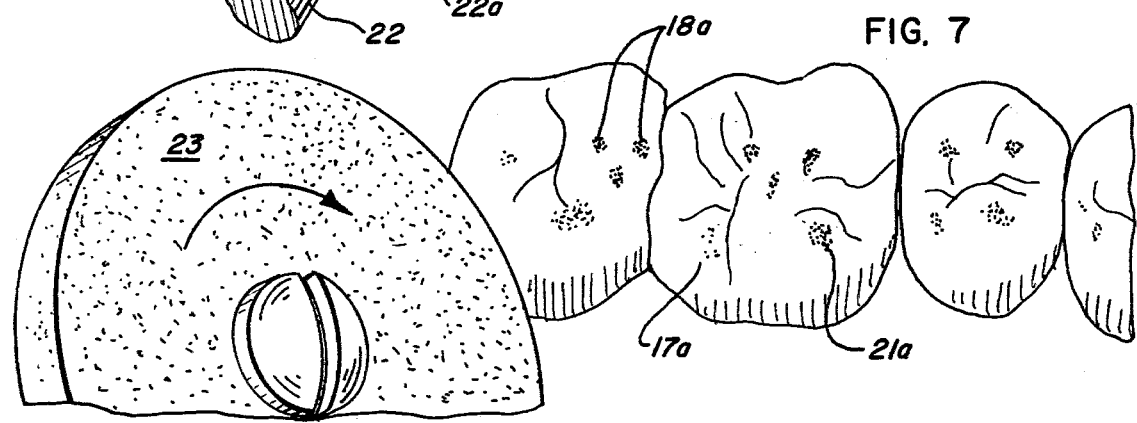
FIG. 7 is an enlarged fragmentary perspective view similar to FIG. 5 but showing three contrasting color marks on the occlusal surface of the porcelain crowns and with one of the marked crown surfaces being engaged by a grinding wheel.

Referring now to the drawings and more particularly to FIG. 1, an upper full mouth impression molding 10 is shown in occluding relation with a lower full mouth dental restorative 11. The molding and restorative in the illustrated embodiment are mounted on an articulating device 12 which can duplicate various movements and/or relations of the natural jaw sections. The type of articulating device may vary from that shown without departing from the scope of the claimed invention. Accordingly, the various components of device 12 14, not be described in detail. Suffice to say, however, that both the molding 10 and restorative 11 are secured to separate plate-like members 13, 14 respectively, which are interconnected to one another by an adjustable hinge assembly 15. The side of each member opposite from the hinge assembly 15 is engaged by an adjustable clamp unit 16. Both the hinge assembly 15 and the clamp unit 16 permit the members 13, 14 to be adjusted relative to one another so that the molding 10 and the restorative 11 can simulate certain jaw movements and/or relations (e.g., centric occlusion, lateral excursion, and protrusive excursion).

In practicing one form of the improved method, the molding 10 and restorative 11 are adjusted to an open position so as to fully expose the occluding surfaces thereof. In the restorative 11 shown in FIG. 1, porcelain crowns are being shaped so as to make proper biting contact with the natural teeth of the upper jaw section, the latter being represented by the molding 10. As seen in FIG. 3, a transferable coating 17 of a first contrasting color (e.g., red) is applied by a brush 18 or similar means to a first predetermined area of the occlusal surface of molding 10. The first predetermined area of the occlusal surface appears in the illustrated embodiment to be substantially the entire occlusal surface. Such a condition need not exist and in lieu thereof the first predetermined area may consist of several small surface segments wherein cusps are located. The thickness of the first coating is very small and approximates five microns. After the first coating has been applied, the molding 10 and restorative 11 are brought into occluding relation by the plate-like member 13 being pivoted about the hinge assembly 15 into the position shown in FIG. 1 and the clamp unit 16 adjusted so as to hold the occluding surfaces in a normal fixed relation and simulate the biting force normally existant between the jaw sections. While the molding 10 and restorative 11 are in occluding relationship a visual inspection of the biting contact can be made.

After the visual inspection of the initial occluding relationship has been made, clamp unit 16 is adjusted to a release position, once again exposing both occlusal surfaces. It will be observed at this time that the exposed occlusal surface of the restorative will have thereon one or more dots or blots 17a of the first coating which represent contact points within an area corresponding to the first predetermined area on the occlusal surface of the molding 10.

It is then optional whether the first coating is removed from the occlusal surface of the molding 10 before a transferable second coating 18 of a second contrasting color (e.g., green) is applied to a second predetermined area of the molding occlusal surface. Because the second predetermined area normally consists of a plurality of petite surface segments, the use of an applicator 20 having a pointed or tapered end 20a is preferred.

Subsequent to the second coating being applied, the molding 10 and restorative 11 are once again brought into an occluding relationship as previously described. Upon releasing the molding and restorative from the second occluding relationship, imprints 18a of the second coating will appear on the restorative occlusal surface which represent contact points located in an area corresponding to the second predetermined area of the molding occlusal surface.

The second coating on the surface of the molding 10 may be removed, if desired, before a transferable coating 21 of a third contrasting color (e.g., yellow) is applied to a third predetermined area of the occlusal surface of the molding 10. As in the case of the second predetermined area, the third predetermined area normally consists of a plurality of petite surface segments disposed intermediate the cusps and the fossa and, thus, an applicator 22 having a pointed end 22a, similar to applicator 20, is recommended for applying the third coating. After the third coating has been applied, the molding 10 and the restorative 11 are once again brought into an occluding relationship and upon release therefrom, the occlusal surface of the restorative will bear imprints 21a of the third coating which represent contact points within an area corresponding to the third predetermined area of the occlusal surface of the molding.

As in the case of the first coating, the second and third coatings are very thin (e.g., five microns or less) so as not to impair the accuracy of the biting contact. Furthermore, the compositions of the coatings are substantially the same except for the color of the dye ingredient. It should also be noted that each coating retains a moist character enabling the transferability thereof to remain intact over a prolonged period of time. Thus, in instances where the coating is not removed from the molding after each occlusion, repeated movement of the molding into occluding relation can occur without requiring re-coating of the occlusal surface of the molding. The composition of the coating material is the subject of applicant's pending application filed concurrently herewith and entitled Coating Compositions, Ser. No. 870,655.

Once all the contact points have been identified by various color markings on the occlusal surface of the restorative 11, the technician by means of a grinding disc 23 or the like removes the undesirable contact points so as to obtain the proper contour whereby a correct bite contact will result and the incidents of paradental diseases such as pyorrhea alveolaris, or the like, due to imperfect bite contact will be eliminated.

The improved method up to this point has been described with regard to the fabrication of a dental restorative; however, the term "dental restorative" is intended to cover a situation where only natural teeth are involved and improved occlusion between certain, or all, of the teeth is required. In such a situation, the required number of coatings is applied to one of the occlusal surfaces of either an upper or lower natural tooth in a manner as previously described with regard to the impression molding 10. It should be noted that the coating material is not injurious to the patient's health. Once the necessary markings have been made and contouring of the occlusal surface has been complete, any residue of the coating material within the patient's mouth can be removed by one of many mouthwashes normally used by dentists.

In practicing the improved method, as aforedescribed, it may be desirable to apply all of the required coatings to one of the occlusal surfaces before the coated surface is brought into biting contact with the other occlusal surface. Furthermore, if desired, removal by grinding or the like of undesirable contact points, identified by the color markings of one coating on the occlusal surface, may occur before successive coatings are applied.

Thus, it will be seen that an improved method has been provided which facilitates the accurate contouring of an occlusal surface of either a natural tooth or a dental restorative. The improved method allows the dentist or technician to readily observe the three dimension contact between the occluding surfaces. Furthermore, when the improved method is being practiced on natural teeth, the patient does not experience discomfort or fatigue.

I claim:

1. A method of marking contact points on an occlusal surface of at least one pair of occluding teeth, said method comprising applying a predetermined number of transferable coatings of contrasting colors on predetermined areas of the occlusal surface of one tooth of the pair, and bringing the one tooth into occluding relation with the second tooth of the pair whereby portions of the previously applied coatings in the predetermined areas of the one tooth are transferred to corresponding predetermined areas of the occlusal surfaces of the second tooth of the pair only at the points of contact located in the corresponding predetermined areas of the second tooth, one of the corresponding predetermined areas of the second tooth occlusal surface including a cusp portion and a second of the corresponding predetermined areas of the second tooth occlusal surface including a fossa portion.

2. The method of claim 1 wherein a plurality of transferable coatings are successively applied to the one occlusal surface, and the pair of teeth are brought into occluding relation after the application of each coating.

3. The method of claim 2 wherein the coating applied to the one occlusal surface is removed therefrom after each movement of the pair of teeth into occluding relation.

4. A method of utilizing a plurality of contrasting colors for marking contact points within a plurality of predetermined areas on an occlusal tooth surface of a pair of occluding teeth, said method comprising applying a transferable coating of a first contrasting color on a first predetermined area of the occlusal surface of one tooth of the pair of occluding teeth; bringing the pair of teeth into a first occluding relation whereby a portion of said coating is transferred to a corresponding first predetermined area of the occlusal surface of the second tooth of the pair only at each point of contact within the corresponding first predetermined area, the latter area of the second tooth occlusal surface including a cusp portion; applying a transferable coating of a second contrasting color on a second predetermined area of the one tooth occlusal surface; and bringing said pair of teeth into a second occluding relation whereby a portion of the second color coating is transferred to a corresponding second predetermined area of the second tooth occlusal surface only at each point of contact within said corresponding said predetermined area, the latter area of the second tooth occlusal surface including a fossa portion.

5. The method of claim 4 wherein the first contrasting color coating is removed from the first predetermined area of the one tooth occlusal surface before the second contrasting color coating is applied to the second predetermined area.

6. The method of claim 4 wherein the first predetermined area is substantially greater in size than the second predetermined area.

7. The method of claim 6 wherein the first coating is applied by a brush.

8. The method of claim 1 wherein each applied coating has a thickness not exceeding substantially five microns.

9. The method of claim 4 wherein at least the one tooth of the pair is a natural tooth impression molding and the second tooth of the pair is a dental restorative having the occluding surface thereof formed in a porcelain crown.

10. The method of claim 9 wherein the impression molding and the dental restorative are mounted on an articulating device.

11. The method of claim 4 wherein a coating of a third contrasting color is applied to a third predetermined area of the one tooth occlusal surface, and said coated one tooth is brought into a third occluding relation whereby a portion of the third color coating is transferred to a corresponding third predetermined area of the second tooth occlusal surface only at each point of contact within said corresponding third predetermined area, said corresponding third predetermined area including a portion of the second tooth occlusal surface intermediate said cusp portion and said fossa portion.

12. The method of claim 4 wherein upon said pair of teeth being brought into the first occluding relation centric contact points are generated; and upon said pair of teeth being brought into the second occluding relation lateral excursion contact points are generated.

* * * * *

UNITED STATES PATENT AND TRADEMARK OFFICE
CERTIFICATE OF CORRECTION

PATENT NO. : 4,183,139
DATED : January 15, 1980
INVENTOR(S) : ASAMI TANAKA

It is certified that error appears in the above-identified patent and that said Letters Patent are hereby corrected as shown below:

Column 2, line 64 — delete "14" and insert therefor --will--

Signed and Sealed this

Twentieth Day of May 1980

[SEAL]

Attest:

SIDNEY A. DIAMOND

Attesting Officer     Commissioner of Patents and Trademarks